United States Patent [19]

Koster et al.

[11] 3,968,109

[45] July 6, 1976

[54] PRODUCTION OF 2-(THIO SUBSTITUTED)CEPHALOSPORIN SULFOXIDES AND 2-(THIO SUBSTITUTED)CEPHALOSPORINS

[75] Inventors: William Henry Koster, Pennington; Joseph Edward Dolfini, Princeton, both of N.J.

[73] Assignee: E. R. Squibb & Sons, Inc., Princeton, N.J.

[22] Filed: Nov. 23, 1973

[21] Appl. No.: 418,520

[52] U.S. Cl.............................. 260/243 C; 424/246
[51] Int. Cl.². ............... C07D 501/04; C07D 501/18
[58] Field of Search ................................. 260/243 C

[56] References Cited
UNITED STATES PATENTS 3,660,395   5/1972   Wright et al. ................... 260/243 C
3,852,282   12/1974   Dolfini ........................... 260/243 C Primary Examiner—Paul M. Coughlan, Jr.
Attorney, Agent, or Firm—Lawrence S. Levinson; Merle J. Smith

[57] ABSTRACT

A new method of producing 2-(thio substituted) cephalosporin derivatives comprises treating a cephem sulfoxide with an electrophilic sulfur reagent in the presence of a strong base. The cephem sulfoxides produced by this step are useful as intermediates, which by reduction of the sulfoxide group, yield 2-(thio substituted) cephalosporins having useful antimicrobial activity.

19 Claims, No Drawings

PRODUCTION OF 2-(THIO SUBSTITUTED)CEPHALOSPORIN SULFOXIDES AND 2-(THIO SUBSTITUTED)CEPHALOSPORINS

SUMMARY OF THE INVENTION

This invention relates to a new method for the production of new 2-(thio substituted) cephalosporin sulfoxides of the formula

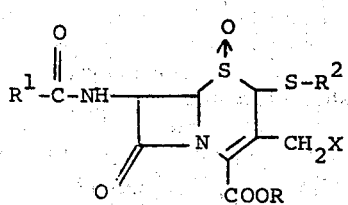

the meaning of the symbols being defined below. The new method comprises thiolating a cephalosporin sulfoxide of the above formula, but without a substituent in the 2-position, with an electrophilic sulfur reagent of the formula $R^2$—S—Y in the presence of a strong base. Reduction of the compound of formula I with a phosphorus halide, tin halide or alkali metal iodide-acetyl halide reagent yields a 2-(thio substituted) cephalosporin derivative with antimicrobial activity.

DETAILED DESCRIPTION OF THE INVENTION

The invention relates to a process for the production of antimicrobial cephalosporin derivatives characterized by a substituted thio radical in the 2-position.

According to this invention a cephalosporin sulfoxide of the following formula is used as the starting material

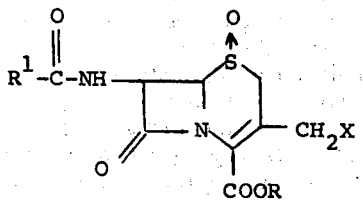

The symbols have the following meanings in formula I and throughout this specification:

R forms a protecting ester group, e.g., R is a lower alkyl group such as t-butyl, a lower alkoxybenzyl group such as p-methoxybenzyl, nitrobenzyl, a halo-lower alkyl group such as 2,2,2-trichloroethyl or a lower alkyl silyl group such as trimethylsilyl. Each of the named groups constitutes a preferred embodiment, especially the t-butyl group. When the protecting group is removed, as discussed below, R is hydrogen.

$R^1$ is hydrogen, lower alkyl, phenyl, phenyl-lower alkyl, e.g., benzyl, phenethyl, α-aminophenyl-lower alkyl, e.g., α-aminobenzyl, α-hydroxyphenyl-lower alkyl, phenoxy-lower alkyl, (e.g., phenoxymethyl); phenylthio-lower alkyl, (e.g., phenylthiomethyl); pyridylthio-lower alkyl, (e.g., pyridylthiomethyl); lower alkoxy-lower alkyl, (e.g., methoxymethyl, ethoxymethyl, propoxyethyl,); lower alkylthio-lower alkyl, (e.g., methylthioethyl, ethylthiomethyl); heterocyclic-lower alkyl, such as pyridyl-lower alkyl, (e.g., pyridylmethyl), thienyl, thenyl, furylmethyl; cyclo-lower alkyl-lower alkyl wherein the cyclo-lower alkyl group has 4 to 6 carbons, preferably 5 to 6, (e.g., cyclopentylmethyl, cyclohexylethyl); α-amino cyclo-lower alkadiene-lower alkyl, wherein the cyclo-lower alkadiene group has 5 or 6 carbons (e.g., α-aminocyclohexadienylmethyl, α-aminocyclopentadienylmethyl). The cyclic phenyl, thienyl, pyridyl, cycloalkyl and cycloalkadienyl groups can also be substituted with one or two lower alkyl, lower alkoxy, halo, nitro, amino or trifluoromethyl groups.

X is hydrogen, lower alkoxy, (lower alkanoyloxy) or lower alkylthio.

The lower alkyl groups referred to above are the one to seven carbon straight or branched chain hydrocarbon groups like methyl, ethyl, propyl, isopropyl, butyl, isobutyl, t-butyl and the like. The first four members, and especially the first two, are preferred.

The lower alkoxy, lower alkylthio and carboalkoxy groups are composed of similar radicals.

The four common halogens are included in the term "halo", but chlorine and bromine are preferred.

The lower alkanoyloxy groups include the acyl radicals of the lower fatty acids having up to seven carbons in the acyl radical, e.g., acetoxy, propionoxy, butyroxy, which are preferred, especially the first, as well as pentanoyloxy, isopentanoyloxy, hexanoyloxy, etc.

The starting material of formula I is treated with a thiolating compound in the presence of a strong base. The thiolating agent is any of a varied group of known electrophilic substances which reacts with an anion to introduce a substituted sulfur group. These include such substances having one of the formulas $R^2S$-Y or $(R^2S)_2$ respectively.

$R^2$ is lower alkyl, substituted lower alkyl wherein the substituent is halo or lower alkoxy, phenyl or substituted phenyl wherein the phenyl substituent is halo, lower alkoxy, nitro, cyano or carbo-lower alkoxy. Y is a halogen, preferably chlorine or bromine, or a sulfonyl radical, e.g., —$SO_2$—Z, wherein Z is lower alkyl, lower alkylcarbonylthio, e.g., methoxycarbonylthio, lower alkylthio, e.g., methylthio, ethylthio, etc. About one equivalent or more of the electrophilic thiolating agent is used.

The reaction is carried out in the presence of a strong base, preferably organometallic base, especially of the alkali metals. These include alkali metal lower alkoxides like potassium t-butoxide, sodium methoxide or lithium methoxide, lithium aryls like triphenylmethyl lithium, lithium lower alkylamides like lithium diisopropylamide, lithium cyclohexyl isopropylamide or sodium cyclohexyl isopropylamide, or alkali metal hydrides like sodium hydride.

The starting material, thiolating agent and strong base are preferably caused to react in a solvent which does not interfere with this reaction by interacting with the thiolating agent or the reactive centers present in the cephalosporin substrate. Examples are such inert organic solvents as t-butanol, dioxane, dimethoxyethane, tetrahydrofuran, methylene chloride, dimethylformamide, benzene, toluene, nitrobenzene and dimethyl ether. Anhydrous conditions are preferred. Temperatures for the reaction range from −78°C to +30°C. The preferred range is normally −30° to +30°C.

This process generally involves the generation of the anion from the cephem sulfoxide starting material and the electrophilic reagent then reacts to introduce the electrophilic sulfur substituent in the 2-position. In a preferred form of the process, the anion is generated from the sulfoxide under anhydrous conditions using the strong base. The temperature is then lowered and the electrophilic sulfur reagent is added. The disappearance of the color of the anion is indicative of complete reaction.

The product of this reaction has the formula

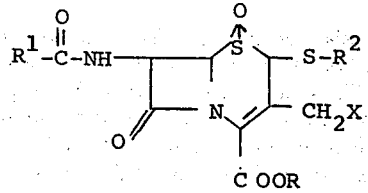

These new intermediates are converted to 2-(thio-substituted) cephalosporin derivatives of the formula

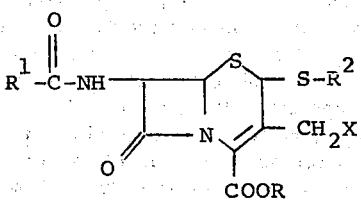

by reduction under conditions that do not effect reduction of the amine or β-lactam carbonyls or the 3,4-double bond. This reduction is effected in the presence of a chemical reducing agent such as phosphorus halides, e.g., phosphorus trichloride or phosphorous tribromide, an acyl halide like acetyl chloride together with an alkali metal dithionite like sodium dithionite or a stannous halide like stannous chloride, or alkali metal iodide-fatty acid-acid halide like potassium or sodium iodide-acetic acid-acetyl chloride as described in J. Org. Chem. 35, 2430 (1970). Solvents for the reduction reaction include those named above, mainly dimethylformamide, dioxane, dimethoxyethane, tetrahydrofuran, benzene, toluene or diethyl ether.

The process steps described above are preferably performed on compounds wherein R forms a protective ester group as defined above. The products, however, are particularly useful as antimicrobial agents in the form of the free acid or as a salt with an alkali or alkaline earth metal or an amine such as benzathine or procaine. Such forms are obtained by converting the easily removed protecting group by conventional means.

A modification of the process of this invention provides additional flexibility in varying the $R^1$ radical of the acylamido substituent in the 7-position. According to this modification, a compound corresponding to formula I but having a triphenylmethyl group on the 7-amino instead of the acyl group $R^1$—CO— is thiolated as described. The corresponding product of formula II (with the triphenylmethyl group as the 7-substituent) is obtained. The latter is treated to hydrolyze the triphenylmethyl group, e.g., with an acid like p-toluenesulfonic acid, hydrochloric acid, hydrobromic acid or the like to obtain the product of formula (IV)

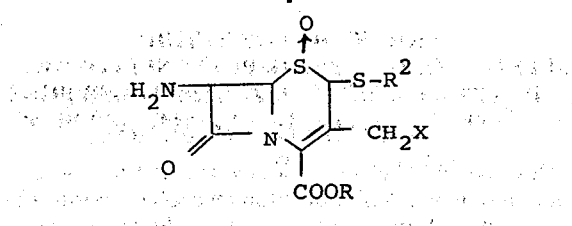

An acyl group $R^1$—CO—, which may otherwise be sensitive to the conditions of the thiolation reaction is now introduced onto the 7-amino group by a conventional acylation procedure, e.g., by treatment with an acid $R^1COOH$ or protected form thereof or acid halide $R^1$—CO—hal or acid anhydride $(R^1CO)_2O$ in an inert organic solvent like tetrahydrofuran. The product of this reaction now conforms to formula II and is treated as described above.

In all of the foregoing, preferred groups represented by the symbols are as follows: R is lower alkyl, especially t-butyl, trichloroethyl, phenyl-lower alkyl, especially benzyl, nitrophenyl-lower alkyl, especially nitrobenzyl and lower alkoxyphenyl-lower alkyl, especially methoxybenzyl, $R^1$ is lower alkyl, especially ethyl, phenyl, phenyl-lower alkyl, especially benzyl, α-aminophenyl-lower alkyl, especially α-aminobenzyl, α-hydroxyphenyl-lower alkyl, especially α-hydroxybenzyl, phenoxy-lower alkyl, especially phenoxymethyl and secondarily thienylmethyl, furfurylmethyl, phenylthio-lower alkyl, especially phenylthiomethyl, pyridyl-lower alkyl, especially pyridylmethyl and α-amino cyclohexadienyl-lower alkyl, especially α-aminocyclohexadienyl methyl, $R^2$ is lower alkyl, especially methyl or ethyl, lower alkoxy-lower alkyl, especially methoxymethyl or ethoxymethyl, phenyl-lower alkoxyphenyl, especially methoxyphenyl, Y is halogen, especially chlorine or bromine or lower alkylsulfonyl, X is hydrogen, lower alkanoyloxy, especially acetoxy or lower alkylthio, especially methylthio or ethylthio, and Z is lower alkyl or lower alkylthio.

The products which are prepared by the process of this invention are useful against gram-positive bacteria, such as *Staphylococcus aureus* and *Streptococcus pyogenes*, and especially against gram-negative bacteria such as *Escherichia coli* and *Proteus vulgaris* when formulated and administered conventionally, for example, in a manner as described in U.S. Pat. No. 3,673,183.

The following examples are illustrative of the invention and constitute preferred embodiments. All temperatures are on the centigrade scale.

EXAMPLE 1

2-(Methylthio)-7-(phenoxyacetamido)-3-desacetoxy cephalosporanic acid methyl ester sulfoxide 7-(Phenoxyacetamido)-3-desacetoxy cephalosporanic acid methyl ester sulfoxide (720 mg., 1.90 mmol.) is suspended in anhydrous dimethoxyethane (30 ml.) under nitrogen and potassium tert. butoxide (214 mg., 1.90 mmol.) is added at room temperature. After dissolution of the suspension is complete, the mixture is cooled to −20° to −25° and methylthiomesylate (240 mg., 1.90 mmol.) is added as a solution in dry dimethoxyethane (5 ml.). The cold bath is removed and the mixture is allowed to warm to room temperature for 1 hour. Removal of solvent in vacuo yields a residue, which is taken up in methylene chloride, washed with water, and the organic layer dried over MgSO₄. The solvent is removed on the rotary evaporator yielding a crude oil (862 mg.). Preparative thin layer chromatography on silica gel plates developed in a 3:1 $CHCl_3$:EtOAc mixture separates the mixture. The material with the smallest r.f. value is starting material which crystallizes by trituration with ether (178 mg., m.p. 215° – 215.5°). The desired 2-(methylthio)-7-(phenoxyacetamido)-3-desacetoxycephalosporanic acid methyl ester sulfoxide is obtained as colorless crystals (353 mg.). Recrystallization from ether gives crystals, m.p. 165°–166°, nmr ($CDCl_3$) δ 2.23 and 2.30 (two S's, 6, —$CH_3$ and —$SCH_3$), 3.85 (S,3,—OMc) 4.20 (S,1,$H_2$), 4.55 (S,2,—$CH_2$—), 4.97 (d,1,J=5 Hz,$H_6$), 6.20 (q,1,J=5, 10 Hz, $H_7$), 6.80–7.47 (complexm, 5, aromatic H), 7.92 (d,1,J=10 Hz, NH); ir $CHCl_3$ 3370, 1805, 1735, 1695 cm⁻¹; (M⁺–18), $^m$/e 406 ($C_{18}H_{26}N_2S_2O_6$ = 424).

Anal. Calc'd. for $C_{18}H_{20}O_6N_2S_2$: C, 51.19; H, 4.30; N, 6.63; Found: C, 51.45; H, 4.54; N, 6.83.

EXAMPLE 2

2-(Methylthio)-7-(phenylacetamido)-3-desacetoxy cephalosporanic acid tert. butyl ester sulfoxide 7-(Phenylacetamido)-3-desacetoxy cephalosporanic acid tert-butyl ester sulfoxide (280 mg. 0.693 mmol.) is suspended as a dry amorphous powder in anhydrous dimethoxyethane under an inert atmosphere. The procedure described in Example 1 is followed using potassium tert.-butoxide (83 mg., 0.739 mmol.) and methylthiomesylate (92 mg., 0.728 mmol.). After working up in the same manner, a crude oil is obtained (312 mg.) which is chromatographed on preparative TLC silica gel plates developed in a 2:1 $CHCl_3$:EtOAc mixture. The band with the lowest r.f. value contains starting material (42 mg.) and the following band contains the desired 2-(methylthio)-7-(phenylacetamido)-3-desacetoxycephalosporanic acid t-butyl ester sulfoxide (89 mg.):nmr ($CDCl_3$) δ 1.53 (S,9,—C($CH_3$)₃), 2.23 (S,3,$CH_3$), 2.33 (S,3,$CH_3$), 3.61 (S,2,$CH_2$), 4.12 (S,1,$H_2$), 4.85 (d,1,J=4.5 Hz, $H_6$), 6.07 (q, 1,J=4.5, 9 Hz, $H_7$), 6.92 (d,1,J=9 Hz, NH), 7.31 (S,5,aromatic); 1.0 ($CHCl_3$) 3400,1800,1725,1685 cm⁻¹; M⁺ $^m$/e 450 ($C_2H_{26}N_2O_5S_2$ = 450).

EXAMPLE 3

2-(Methylthio)-7-(phenylacetamido)-3-desacetoxy cephalosporanic acid trichloroethyl ester sulfoxide 7-(Phenylacetamido)-3-desacetoxycephalosporanic acid trichloroethyl ester sulfoxide (672 mg. 1.4 mmol.) is dissolved in dry methoxyethane (20 ml.) and the procedure described in Example 1 is followed using potassium tert.-butoxide (169 mg. 1.4 mmol.) and methylthiomesylate (177 mg. 1.4 mmol). The residue from the reaction mixture is chromatographed on silica gel plates developed in a 1:1 EtOAc:$CHCl_3$ mixture yielding the desired 2-(methylthio)-7-(phenylacetmido)-3-desacetoxycephalosporanic acid trichloromethyl ester sulfoxide as a glass (171 mg.): nmr ($CDCl_3$) δ 2.33 (S,6,—$CH_3$ and $SCH_3$), 3.57 (S,2,—$CH_2$—), 4.28 (S,1,$H_2$), 4.90 (complex m,3,—$CH_2CCl_3$ and $H_6$), 6.08 (q,1,J=5,9 Hz, $H_7$), 7.03 (d,1,J=9 Hz, NH), 7.25 (S,5,aromatic H).

EXAMPLE 4

2-(Methylthio)-7-(phenoxyacetamido)-3-desacetoxy cephalosporanic acid p-methoxybenzyl ester sulfoxide 7-(Phenoxyacetamido)-3-desacetoxy cephalosporanic acid p-methoxybenzyl ester sulfoxide (1.5 g., 3 mmol.) is suspended in anhydrous dimethoxyethane (50 ml.) and the procedure described in Example 1 is followed using potassium tert.-butoxide (336 mg. 3 mmol.) and methylthiomesylate (378 mg., 3 mmol.). After working the reaction up in the same manner, the residue (1.5 g.) is chromatographed on silica gel plates developed in 3:1 $CHCl_3$:EtOAc. The material with the smallest r.f. value is starting material (301 mg.). The desired 2-(methylthio)-7-(phenoxyacetamido)-3-desacetoxy cephalosporanic acid p-methoxybenzyl ester sulfoxide (631 mg.) is found in the following band. Recrystallization from a chloroform-ether mixture yields a solid, m.p. 128°–130° (dec.), nmr ($CDCl_3$) δ 2.27 and 2.32 (two S's,6,—$CH_3$ and —$SCH_3$), 3.87 (S,3,—$OCH_3$), 4.28 (S,1,$H_2$), 4.55 (S,2,—$CH_2CO$), 4.87 (d,1, J=5Hz, $H_6$), 5.24 (S,2,—$OCH_2$—), 6.12 (q,1,J=5, 11Hz, $H_7$), 6.79 – 7.49 (complex m,9,aromatic H), 7.92 (d,1,J=11Hz, NH); ν max 3380, 1800, 1730, 1690 cm⁻¹; λ max 225 mμ (E = 20,670), 270 mμ (E = 12,455);

Anal. Calc'd for $C_{25}H_{26}N_2O_7S_2$: C, 56.59; H, 4.94; N, 5.28; Found: c, 56.64; H, 4.87; N, 5.11.

EXAMPLES 5 to 23

The additional 2-(substituted thio)-7-acylamidocephalosporanic acid ester sulfoxides in Table I are produced by the following procedure.

The cephalosporin sulfoxide ester of formula I is mixed with the solvent indicated and the reaction mixture cooled to 0° to 40°. One equivalent of the base indicated is added, followed by the addition of thiolating agent $R^2$—S—Y. After completion of the reaction, solvents miscible with water are removed under reduced pressure and the mixture is taken up in an organic solvent and washed with water. The organic layer is dried and the solvent is removed in vacuo. The residue is then chromatorgraphed to isolate the desired 2-(S-$R^2$)-7-[($R^2CO$)amido]cephalosporanic acid ester sulfoxide of formula II.

TABLE I

Synthesis of 2-Methylthio Sulfoxide Esters

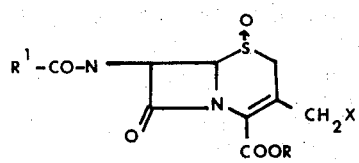
(I)

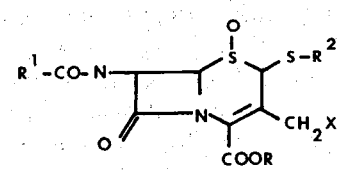
(II)

| Example | R¹ | X | R | R² | Y | base | solvent |
|---|---|---|---|---|---|---|---|
| 5 | φCH₂ | H | —CH₂—C₆H₄—OMe | CH₃ | Cl | NaH | DME |
| 6 | φCH₂ | OAc | —CH₂—C₆H₄—OMe | CH₃ | —SO₂CH₃ | KOt—Bu | DME |
| 7 | φOCH₂ | OAc | —CH₂—C₆H₄—OMe | CH₃ | —SO₂CH₃ | KOt—Bu | DME |
| 8 | CH₃CH₂ | OAc | —CH₂—C₆H₄—NO₂ | CH₃CH₂ | —SCH₂CH₃ | BuLi | THF |
| 9 | (2-thienyl)CH₂ | H | —CH₂CCl₃ | CH₃ | SO₂—φ | NaNH₂ | Dioxane |
| 10 | (2-thienyl)CH₂— | OAc | —CH₂—φ | CH₃ | —SCH₃ | LiN[CH(CH₃)₂]₂ | THF |
| 11 | φ—CH(OH)— | OAc | —CH₂CCl₃ | φ | Cl | φLi | DME |
| 12 | φ—CH(NH-t-BOC)— | H | —CH₂CCl₃ | CH₃CH₂CH₂— | Cl | NaH | DME |
| 13 | (2-pyridyl)CH₂CO— | OAc | —CH₂CCl₃ | MeO—C₆H₄— | Cl | BuLi | Dioxane |
| 14 | H | H | —CH₂—φ | —CH₂CH₂CH₃ | Cl | KOt—Bu | DME |
| 15 | (2-furyl)CH₂— | OAc | —CH₂—C₆H₄—NO₂ | φCH₂— | Br | KOt—Bu | THF |
| 16 | φSCH₂— | OAc | —CH₂—C₆H₄—OMe | CH₃ | SO₂—C₆H₄—CH₃ | BuLi | DME |
| 17 | φ₃C— | OAc | —CH₂—C₆H₄—OMe | CH₃ | SCH₃ | KOt—Bu | DMF |
| 18 | φ₃C— | OAc | t-butyl | CH₃ | SO₂CH₃ | KOt—Bu | DME |
| 19 | φ₃C— | OAc | CH₂CCl₃ | CH₃ | SO₂CH₃ | KOt—Bu | DME |
| 20 | φ₃C— | OAc | CH₂—φ | CH₃ | SO₂CH₃ | KOt—Bu | DME |
| 21 | φ₃C— | OAc | CH(φ)₂ | CH₃ | Cl | KOt—Bu | DME |
| 22 | φ₃C— | H | CH₂—C₆H₄—NO₂ | CH₃ | SO₂CH₃ | KOt—Bu | DME |
| 23 | φ₃C— | H | CH₂—C₆H₄—OMe | CH₃ | SO₂CH₃ | KOt—Bu | DME |

EXAMPLE 24

7-Amino-2-(methylthio)cephalosporanic acid-p-methoxybenzyl ester sulfoxide 2-(Methylthio)-7-(N-triphenylmethyl)aminocephalosporanic acid p-methoxybenzyl ester sulfoxide (709 mg., 1.0 mmol.) is dissolved in acetone (25 ml.) and cooled to 0°. One equivalent of p-toluenesulfonic acid monohydrate (190 mg., 1 mmol.) is added to the mixture while stirring. The reaction mixture is allowed to slowly warm to room temperature over a 3 hour period. The solvent is removed under reduced pressure and the residue is taken up in 5% $NaHCO_3$ solution and methylene chloride. The organic layer is dried over $Na_2SO_4$ and the solvent is removed in vacuo yielding the desired 7-amino-21(methylthio)cephalosporanic acid (p-methoxybenzyl) ester sulfoxide as an oily residue.

EXAMPLE 25

7-Amino-2-(methylthio)cephalosporanic acid t-butyl ester sulfoxide 2-(Methylthio)-7-(N-triphenylmethyl)aminocephalosporanic acid t-butyl ester sulfoxide is hydrolyzed as described in Example 24 yielding the 7-amino-2-(methylthio)cephalosporanic acid t-butyl ester sulfoxide as an oil.

EXAMPLE 26

7-Amino-2-(methylthio)cephalosporanic acid trichloroethyl ester sulfoxide 2-(Methylthio)-7-(N ltriphenylmethyl)aminocephalosporanic acid trichloroethyl ester sulfoxide is hydrolyzed by the method described in Example 24 yielding 7-amino-2-(methylthio)cephalosporanic acid trichloroethyl ester sulfoxide as a glass.

EXAMPLE 27

7-Amino-2-(methylthio)cephalosporanic acid benzyl ester sulfoxide 2-(Methylthio)-7-(N-triphenylmethyl)aminocephalosporanic acid benzyl ester sulfoxide is hydrolyzed as described in Example 24 and 7-amino-2-(methylthio)-cephalosporanic acid benzyl ester sulfoxide is obtained as an amorphous solid.

EXAMPLE 28

7-Amino-2-(methylthio)cephalosporanic acid benzhydryl ester sulfoxide 2-(Methylthio)-7-(N-triphenylmethyl)-7-aminocephalosporanic acid benzhydryl ester sulfoxide is hydrolyzed using the procedure described in Example 24 yielding 7-amino-2-(methylthio)cephalosporanic acid benzhydryl ester sulfoxide.

EXAMPLE 29

7-Amino-2-(methylthio)-3-desacetoxycephalosporanic acid p-nitrobenzyl ester sulfoxide 2-Methylthiodesacetoxy-7-(N-triphenylmethyl)aminocephalosporanic acid p-nitrobenzyl ester sulfoxide is hydrolyzed in the manner described in Example 24 yielding 7-amino-2-(methylthio)-3-desacetoxycephalosporanic acid p-nitrobenzyl ester sulfoxide as a glass.

EXAMPLE 30

7-Amino-2-(methylthio)-3-desacetoxycephalosporanic acid p-methoxybenzyl ester sulfoxide 2-(Methylthio)-3-desacetoxy-7[(N-triphenylmethyl)amino]cephalosporanic acid p-methoxybenzyl ester sulfoxide is hydrolyzed using the procedure described in Example 24 yielding 7-amino-2-(methylthio)-3-desacetoxycephalosporanic acid p-methoxybenzyl ester sulfoxide.

EXAMPLE 31

2-(Methylthio)-7-phenylacetamidocephalosporanic acid trichloroethyl ester sulfoxide 7-Amino-2-(methylthio)cephalosporanic acid trichloroethyl ester sulfoxide (477 mg., 1.0 mmol.) is dissolved in 30 ml. of methylene chloride and the solution is cooled to 0°–5°. While stirring triethylamine (140 ml., 1.0 mmol.) is added followed by the addition of phenylacetyl chloride 155 mg., 1.0 mmol.). The mixture is stirred for 1 hr. at 0°–5°, then the reaction mixture is washed with water, followed by washing with pH 3.5 buffer solution. After drying ($NaSO_4$) the solvent is removed in vacuo yielding the product, 2-methylthio)-7-phenylacetamidocephalosporanic acid trichloroethyl ester sulfoxide as an amorphous solid.

EXAMPLE 32

2-(Methylthio)-7-(phenoxyacetamido)-3-desacetoxycephalosporanic acid p-nitrobenzyl ester sulfoxide 7-Amino-2-(methylthio)-3-desacetoxycephalosporanic acid p-nitrobenzyl ester sulfoxide is acylated with phenoxyacetyl chloride using the procedure described in Example 31 yielding the product 2-(methylthio)-7-(phenoxyacetamido)-3-desacetoxy cephalosporanic acid p-nitrobenzyl ester sulfoxide as an amorphous solid.

EXAMPLE 33

2-(Methylthio)-7-[2-(2-thienyl)acetamido]cephalosporanic acid t-butyl ester sulfoxide 7-Amino-2-(methylthio)cephalosporanic acid t-butyl ester sulfoxide is acylated with (2-thienyl)acetyl chloride using the procedure described in Example 31 yielding the product 2-(methylthio)-7-[2-(2-thienyl)acetamido]cephalosporanic acid t-butyl ester sulfoxide as a glass.

EXAMPLE 34

7-[2-(N-tert-butoxycarbonyl)amino-2-(1,4-cyclohexadienyl)acetamido]-2-(methylthio)cephalosporanic acid-(p-methoxybenzyl) ester sulfoxide A solution of 2-[N-(tert-butoxycarbonyl)amino]-2-(1,4-cyclohexadienylacetic acid (2.53 g., 0.01 mol.) in THF (50 ml.) containing triethylamine (2.02 g., 0.02 mol.) is cooled to −10°. While stirring vigorously, isobutyl chloroformate is added over a period of 1 minute. The slurry is mixed at −5° for 15 minutes. To this is added a cold solution of 7-amino-2-(methylthio)cephalosporanic acid p-methoxybenzyl ester sulfoxide (4.54 g., .01 mol.) in THF (30 ml.). The temperature is kept between 0° and −10° for 1 hour and then allowed to rise to 35° for 2 hours. The solvent is removed in vacuo and the residue taken up in ethyl acetate and water. The organic layer is then washed with pH 3.6 buffer solution and dried ($Na_2SO_4$). The solvent is removed under reduced pressure yielding the product 7-[2-(N-tert-butoxycarbonyl)amino-2-(1,4-cyclohexadienyl)acetamido]-2 -(methylthio)cephalosporanic acid (p-methoxybenzyl) ester sulfoxide as a glass.

EXAMPLE 35

7-(N-tert-butoxycarbonyl)amino-2-(1,4-cyclohexadienyl)acetamido]-2-(methylthio)-3-desacetoxycephalosporanic acid (p-methoxybenzyl) ester sulfoxide The procedure described in Example 34 is used to acylate 7-amino-2-(methylthio)-3-desacetoxycephalosporanic acid p-methoxybenzyl ester sulfoxide yielding the product 7-[2-(N-tert-butoxycarbonyl)amino-2-(1,4-cyclohexadienyl)acetamido]-2-(methylthio)-3-desacetoxycephalosporanic acid p-methoxybenzyl ester sulfoxide as a glass.

EXAMPLE 36

7-[2-(N-tert-butoxycarbonyl)amino-2-(phenyl-)acetamido]-2-(methylthio)cephalosporanic acid (p-methoxybenzyl) ester sulfoxide The procedure described in Example 34 is used to acylate 7-amino-2-(methylthio)cephalosporanic acid p-methoxybenzyl ester sulfoxide. However, 2-[N-tert-butoxycarbonyl)amino]-2-phenylacetic acid is used as the precursor to the mixed anhydride and 7-[2-(N-tert-butoxycarbonyl)amino-2-(phenyl)acetamido]-2-(methylthio)cephalosporanic acid p-methoxybenzyl ester sulfoxide is obtained as a foam.

EXAMPLE 37

7-[2-(N-tert-butoxycarbonyl)amino-2-(phenyl-)acetamido]-2-(methylthio)-3-desacetoxycephalosporanic acid p-methoxybenzyl ester sulfoxide The procedure described in Example 36 is used to acylate 7-amino-2-(methylthio)-3-desacetoxycephalosphoranic acid p-methoxybenzyl ester sulfoxide yielding the desired product 7-[2-(N-tert-butoxy carbonyl)amino-2-(phenyl)acetamido]-2-(methylthio)-3-desacetoxycephalosporanic acid p-methoxybenzyl ester sulfoxide as a foam.

EXAMPLE 38

7-Mandelamido-2-(methylthio)cephalosphoranic acid benzhydryl ester sulfoxide

2-Amino-2-methylthio)cephalosporanic acid benzhydryl ester is acylated with mandeloyl chloride using the procedure described in Example 31 yielding the product 7-mandelamido-2-(methylthio)cephalosporanic acid benzhydryl ester sulfoxide as an amorphous solid.

EXAMPLE 39

7-Amino-2-(methylthio)cephalosporanic acid sulfoxide

Procedure A 2-(Methylthio)-7-aminocephalosporanic acid p-methoxybenzyl ester sulfoxide (485 mg., 1.0 mmol.) is dissolved in benzene (75 ml.) and anisole (2.5 ml.) and trifluoroacetic acid (5 ml.) is added. The mixture is stirred at room temperature for 1 hour and solvent is removed in vacuo. The residue is taken up in an ethyl acetate-water mixture and the organic layer separated. The pH of the aqueous layer is adjusted to 4.1 with sodium bicarbonate solution and the aqueous solution is concentrated in vacuo causing separation of the product 2-(methylthio)-7-aminocephalosporanic acid sulfoxide.

Procedure B

2-Methylthio-7-(N-triphenylmethyl)aminocephalosporanic acid sulfoxide (565 mg. 1 mmol.) is dissolved in acetone (50 ml.) and the mixture is cooled to 0°. One equivalent of p-toluenesulfonic acid monohydrate (190 mg. 1 mmol.) is added to the mixture while stirring. The reaction mixture is allowed to warm to room temperature and stirred for 3 hours. The solvent is removed under reduced pressure, the residue taken up in water, and the pH adjusted to 4.1. The aqueous solution is concentrated causing the same produce as in Procedure A to separate.

7-Amino-2-methylthio-3-desacetoxycephalosporanic acid sulfoxide

7-Amino-2-methylthiodesacetoxycephalosporanic acid p-methoxybenzyl ester sulfoxide is treated using the same procedure as in Procedure A above yielding 7-amino-2-methylthio-3-desacetoxycephalosporanic acid sulfoxide.

2-Methylthio-7-(N-triphenylmethyl)amino-3-desacetoxycephalosporanic acid is cleaved as in Procedure B above yielding 7-amino-2-methylthio-3-desacetoxycephalosporanic acid sulfoxide as an amorphous powder.

EXAMPLE 40

2-(Methylthio)-7-[2-(2-thienyl)acetamido]cephalosporanic acid sulfoxide

7-Amino-2-(methylthio)cephalosporanic acid sulfoxide (321 mg., 1 mmol.) is added to 50 ml. of purified chloroform and triethylamine (202 mg. 2 mmol.) is added to the solution. After stirring at room temperature, the mixture is cooled to 0°–5° and 2-(2-thienyl)acetyl chloride (161 mg. 1 mmol.) is added to the mixture, which is then stirred for 2 hours. The reaction mixture is washed with pH 3.5 buffer solution, followed by drying the organic layer over $Na_2SO_4$, and removal of the solvent in vacuo yielding the product, 2-(methylthio)-7-[2-(2-thienyl)acetamido]cephalosporanic acid sulfoxide as a foam.

2-(Methylthio)-7-[2-(2-thienyl)acetamido]-3-desacetoxycephalosporanic acid sulfoxide 7-Amino-2-(methylthio)desacetoxycephalosporanic acid sulfoxide is acylated with 2-(2-thienyl)acetyl chloride by the same procedure described above to obtain 2-(methylthio)-7-[2-(2-thienyl)acetamido]-3-desacetoxycephalosporanic acid sulfoxide.

EXAMPLE 41

2-(Methylthio)-7-phenoxyacetamido 3-desacetoxy cephalosporanic acid sulfoxide 2-(Methylthio)-7-phenylacetamido-3-desacetoxy cephalosporanic acid p-methoxybenzyl ester sulfoxide (525 mg.) is added to benzene (70 ml.) followed by the addition of anisole (2.6 ml.) and trifluoroacetic acid (4.6 ml.). The mixture is stirred at room temperature for 50 minutes. After removal of the solvent under reduced pressure the residue is taken up in ethyl acetate and extracted with cold saturated aqueous sodium bicarbonate solution. The basic solution is separated, acidified to pH 1.5 with dilute hydrochloric acid and the aqueous mixture extracted with ethyl acetate. The solvent is removed in vacuo yielding a solid residue 2-(methylthio)-7-phenoxyacetamido-3-desacetoxy cephalosporanic acid sulfoxide (406 mg.) which is recrystallized from a chloroform ether mixture, m.p. 153°–154°; nmr (CDCl$_3$) δ 2.32 and 2.37 (two S's, 6, —CH$_3$ and —SCH$_3$), 4.42 (S, 1, H$_2$), 4.62 (S, 2,CH$_2$CO), 5.00 (d, 1, J=5Hz, H$_6$), 6.17 (q, 1, J=5, 10Hz, H$_7$ ), 6.69 – 7.46 (complex m, 5 aromatic H) 7.98 (d, 1, J=10Hz, NH) D max (CHCl$_3$) 1800, 1720 (sh), 1695 cm$^{-1}$;

Anal. Calc'd for C$_{17}$H$_{18}$N$_2$O$_6$S$_2$ (410.46): C, 49,74; H, 4.42; N, 6.83. Found: C, 49.92; H, 4.46; N, 7.09.

EXAMPLES 42 to 53

The removal of the protective ester group O-R to obtain the free carboxylic acid group is accomplished by any of several alternative methods. Although the methods have general applicability, certain methods are preferred for the removal of particular esters. A preferred method (A) for the removal of methoxybenzyl esters is illustrated in Example 24.

A preferred method (B) for removal of trichloroethyl ester is as follows:

The cephem trichloroethyl ester (1 molar equivalent) is dissolved in a 5:1 DMF-HOAc mixture and the solution cooled to 0°–5°. Fine zinc dust (10 g-atom equivalents) is added and the resulting mixture is stirred in an ice bath for 1.5 hours. After removal of zinc by filtration, the solution is poured into an ethyl acetate-water mixture, the organic layer separated, and again washed with water. Then, while stirring the organic layer with water the pH is adjusted to 8.5. The aqueous layer is separated, ethyl acetate is added, and the pH is adjusted to 3 with dilute hydrochloric acid. The organic layer is then separated, washed with water, and dried (Na$_2$SO$_4$). Removal of solvent in vacuo yields the free acid.

A preferred method (C) for removal of a benzhydryl ester is as follows:

The ester is dissolved in dioxane to which a trace of dry HCl is added. The catalyst, prereduced 10% Pd-C (twice the weight of ester is added) is suspended in dioxane and the solution of ester is added. The hydrogenolysis is performed at room temperature under an atmosphere of hydrogen. The solvent is removed in vacuo and the workup is performed in ethyl acetate and water as described in Procedure B to yield the free acid.

A preferred method (D) for the removal of a benzyl or nitrobenzyl ester is the same as described in C, but omitting the addition of dry HCl.

A preferred method (E) for removal of a tert-butyl ester is as follows:

The ester is dissolved in either 98–100% formic acid or trifluoroacetic acid at 0°–5°. The solution is allowed to warm to room temperature for 30 minutes and the solvent is removed in vacuo. The residue is then worked up in ethyl acetate and water as described in Procedure B.

The foregoing methods are referred to in Tables II and V, below.

The compounds in the following Table II having the formula IIa in which there is a free carboxyl group in the 4-position are obtained from the compound of formula II by removing the protective ester group O-R according to the foregoing procedure identified in the Table:

TABLE II

| Example | R$^1$ | X | R | R$^2$ | Procedure |
|---|---|---|---|---|---|
| 42 | φCH$_2$— | H | —CH$_2$—⟨⟩—OMe | —CH$_3$ | A |
| 43 | φCH$_2$— | OAc | —CH$_2$—⟨⟩—OMe | —CH$_3$ | A |
| 44 | φOCH$_2$— | OAc | —CH$_2$—⟨⟩—OMe | —CH$_3$ | A |
| 45 | CH$_3$CH$_2$— | OAc | —CH$_2$—⟨⟩—NO$_2$ | CH$_3$CH$_2$— | D |
| 46 | ⟨S⟩—CH$_2$— | H | —CH$_2$CCl$_3$ | —CH$_3$ | B |
| 47 | ⟨S⟩—CH— | OAc | —CH$_2$—⟨⟩ | —CH$_3$ | D |

TABLE II-continued

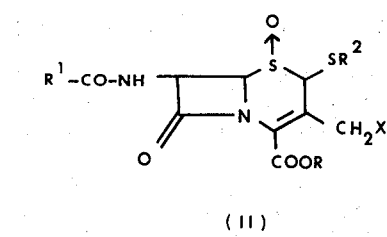

(II)

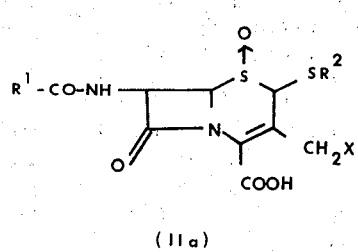

(IIa)

| Example | R¹ | X | R | R² | Procedure |
|---|---|---|---|---|---|
| 48 | (phenyl)-CH(OH)- | OAc | —CH₂CCl₃ | phenyl | B |
| 49 | (furyl)-CH₂- | OAc | -CH₂-C₆H₄-NO₂ | φCH₂ | D |
| 50 | φSCH₂— | OAc | -CH₂-C₆H₄-OMe | —CH₃ | A |
| 51 | (pyridyl)-CH₂- | OAc | —CH₂CCl₃ | MeO-C₆H₄- | B |
| 52 | H | H | -CH₂-phenyl | —CH₂CH₂CH₃ | D |
| 53 | phenyl | OAc | t-Bu | CH₃ | E |

EXAMPLE 54

2-(Methylthio)-7-phenoxyacetamido-3-desacetoxycephalosporanic acid methyl ester (A¹) 2-(Methylthio)-7-phenoxyacetamido-3-desacetoxycephalosporanic acid methyl ester sulfoxide (0.100g.) is dissolved in anhydrous dimethylformamide under an inert atmosphere and cooled to −20° to −25°. While stirring mechanically, 0.3 ml. of phosphorus tribromide is added and the mixture stirred for 40 minutes. Ice cold sodium chloride solution (50 ml.) is added and the mixture is extracted three times with methylene chloride. The combined extracts are washed with cold sodium chloride solution, dried (MgSO₄), and the solvent removed under reduced pressure yielding an oil (0.111 g.). Crystallization from a methylene chloride-ether-n-hexane mixture yields a solid 2-(methylthio)-7-phenoxyacetamido-3-desacetoxycephalosporanic acid methyl ester (0.074 g.), m.p. 128.5°–130°: nmr (CDCl₃) δ 2.25 and 2.26 (two S's, 6,—CH₃ and —SCH₃), 3.87 (S,3,—COOMe) 7.38 (S,1,H₂), 4.58 (S,2,—CH₂CO), 5.40 (d,1,J=5 Hz,H₆), 6.01 (q,1,J=5, 9Hz,H₇), 6.83 – 7.56 (complex m,6, aromatic H and NH); max (CHCl₃) 1790, 1735, 1695 ch⁻¹; M⁺, m/e 408 (C₁₈H₂₀N₂S₂O₅ = 408).

EXAMPLE 55

2-(Methylthio)-7-phenoxyacetamido-3-desacetoxycephalosporanic acid p-methoxybenzyl ester (A²) 2-(Methylthio)-7-phenoxyacetamido-3-desacetoxy cephalosporanic acid p-methoxybenzyl ester sulfoxide (46 mg.) is dissolved in anhydrous dimethylformamide under an inert atmosphere and cooled to −20°. While mechanically stirring the mixture, 0.1 ml. of phosphorus tribromide is added and the mixture is allowed to stir for 15 minutes while the temperature rises to −10°. Ice-cold aqueous saturated sodium chloride solution is added to the reaction mixture and the product is extracted with methylene chloride. The extracts are dried (Na₂SO₄) and the solvent is removed under reduced pressure yielding the product 2-(methylthio)-7-phenoxyacetamido-3-desacetoxycephalosporanic acid (p-methoxybenzyl)ester as an oil (38 mg.): nmr (CDCl₃) δ 2.20 and 2.24 (two S's,6,—CH₃ and —SCH₃), 3.78 (s,3,—OCH₃), 4.32 (s,1,H₂), 4.53 (s,2,—CH₂CO), 5.20 (s,2,—OCH₂), 5.32 (d,1,J=5.5Hz,H₆), 5.93 (q,1,J=5.5,9Hz,H₇),6.73 – 7.50 (complex m, 10, aromatic H and NH); max (CHCl₃) 1785, 1725, 1695 cm⁻¹.

EXAMPLES 56 to 79

In addition to the procedures described in Examples 53 to 54, 2-(substituted thio)cephem sulfoxide esters are reduced by the following alternate procedures:

(B¹) A molar equivalent of the cephem sulfoxide is dissolved in a 2:1 mixture of acetonitrile-DMF and the solution is cooled to —40°. Then finely powdered anhydrous stannous chloride (1.25 molar equivalents) is added with stirring followed by acetyl chloride (5 molar equivalents). The mixture is stirred for 1 hour at 0°-5° and then 1 hour at room temperature. After removal of the solvent in vacuo, an ethyl acetate —H₂O mixture is added to the residue. The organic layer is washed with 3% HCl solution, followed by a 5% NaHCO₃ solution and then with water. After drying (Na₂SO₄), the solvent is removed under reduced pressure yielding the desired product.

(C¹) A molar equivalent of the cephem sulfoxide is dissolved in DMF and sodium dithionite(4 molar equivalents) is added. The mixture is cooled to 0°-5° and acetyl chloride (5-molar equivalents) added dropwise to the reaction mixture. After stirring in the cold for 30 minutes the mixture is poured into saturated sodium bicarbonate and extracted with ethyl acetate. The organic extract is washed with water, dried (Na₂SOhd 4), and the solvent removed in vacuo yielding the desired product.

TABLE III

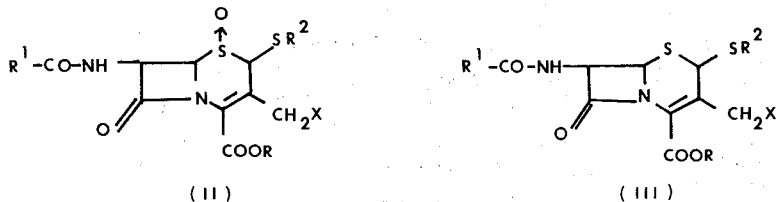

| Example | R¹ | X | R | R² | Procedure |
|---|---|---|---|---|---|
| 56 | φCH₂ | H | CH₂-⟨⟩-OMe | —CH₃ | A¹ |
| 57 | φCH₂— | OAc | -CH₂-⟨⟩-OMe | —CH₃ | A¹ |
| 58 | φOCH₂— | OAc | -CH₂-⟨⟩-OMe | —CH₃ | C¹ |
| 59 | CH₃CH₂— | OAc | -CH₂-⟨⟩-NO₂ | CH₃CH₂ | B¹ |
| 60 | [S]-CH₂- | H | —CH₂CCl₃ | —CH₃ | A² |
| 61 | [S]-CH₂- | OAc | -CH₂-⟨⟩ | —CH₃ | B¹ |
| 62 | ⟨⟩-CH(OH)- | OAc | —CH₂CCl₃ | ⟨⟩ | C¹ |
| 63 | ⟨⟩-CH(NH-t-BOC)- | H | —CH₂CCl₃ | CH₃CH₂CH₂ | A¹ |
| 64 | [N]-CH₂- | OAc | —CH₂CCl₃ | MeO-⟨⟩- | C¹ |
| 65 | H | H | CH₂-⟨⟩ | —CH₂CH₂CH₃ | B¹ |
| 66 | ⟨⟩- | OAc | t-Bu | CH₃ | C¹ |
| 67 | ⟨⟩-CH₂- | H | —CH₂—OC(=O)(CH₃)₃ | Br-⟨⟩- | A¹ |
| 68 | φOCH₂— | OAc | CH₂-⟨⟩- | CH₃ | A¹ |
| 69 | φCH₂— | H | —CH₂OC(=O)OH₃ | φCH₂— | A¹ |
| 70 | [O] | OAc | -CH₂-⟨⟩-NO₂ | φCH₂— | A¹ |

TABLE III-continued

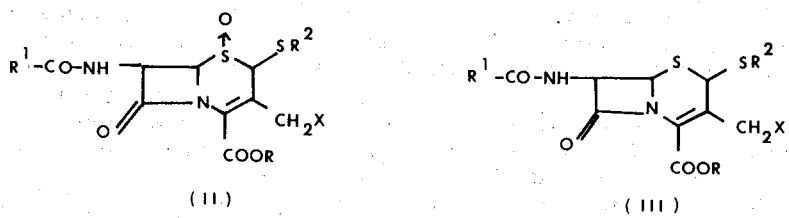

(II.)   (III)

| Example | R¹ | X | R | R² | Procedure |
|---|---|---|---|---|---|
| 71 | φSCH₂— | OAc | —CH₂—⟨⟩—OMe | —CH₃ | A² |
| 72 | φ₃C— | OAc | —CH₂—⟨⟩—OMe | —CH₃ | A¹ |
| 73 | φ₃C— | OAc | tert-butyl | —CH₃ | C¹ |
| 74 | C₂H₅OCH₂— | OAc | —CH₂CCl₃ | —CH₃ | B¹ |
| 75 | φ₃C— | OAc | CH₂—⟨⟩ | CH₃ | B¹ |
| 76 | φ₃C— | OAc | —CH(φ)(φ) | CH₃ | B¹ |
| 77 | CH₃SCH₂— | H | CH₂—⟨⟩—NO₂ | CH₃ | A¹ |
| 78 | φ₃C— | H | —CH₂—⟨⟩—OMe | CH₃ | B¹ |
| 79 | ⟨⟩—CH(OH) | OAc | —CH(φ)(φ) | CH₃ | B¹ |

EXAMPLE 80

2-(Methylthio)-7-(phenoxyacetamido)-3-desacetoxycephalosporanic acid (A²) 2-(Methylthio)-7-(phenoxyacetamido)-desacetoxycephalosporanic acid sulfoxide (120 mg.) is dissolved in anhydrous dimethylformamide (7 ml.) and cooled to —20°. While stirring mechanically, phosphorus tribromide (0.26 ml.) is added and the mixture stirred at —20° for 45 minutes. An ice cold solution of 5% $(NH_4)_2 HPO_4$ in water is added to the reaction mixture. The aqueous solution is acidified to pH 2.5 and extracted with ethyl acetate. The organic solution is extracted with sodium bicarbonate, the aqueous solution acidified to pH 1.5, and the desired 2-(methylthio)-7-(phenoxyacetamido)-3-desacetoxycephalosporanic acid is extracted with ethyl acetate. Removal of the solvent under reduced pressure yields a residue (90 mg.) which is triturated with an ether-hexane mixture yielding a colorless solid, m.p. 163°–165° dec., nmr $(CDCl_3)$ δ 2.30 (s,6,—CH₃ and —SCH₃), 4.38 (s,1,H₂), 4.61 (s,2,CH₂CO), 5.39 (d,1,J=5Hz,H₆), 6.00 (q,1,J=5, 9Hz), 6.87 – 7.52 (comples m, aromatic H and NH); νmax $(CHCl_3)$, 1785, 1720 (sh) 1695 cm⁻¹.

(B²) The procedure described in Example 55 is used to reduce 2-(methylthio)-7-(phenoxyacetamido)-3-desacetoxycephalosporanic acid sulfoxide to yield material identical to that prepared by Procedure A².

The following are alternate methods for the reduction of 2-(substituted thio)-7-(acylamido)cephalosporanic acid sulfoxides to the corresponding 2-(substituted thio)-7-(acylamido)cephalosporanic acid:

(C²) A molar equivalent of the cephem sulfoxide is dissolved in a 2.1 mixture of acetonitrile-DMF and the solution cooled to —40°. Finely powdered anhydrous stannous chloride (1.25 molar equivalents) is added with stirring followed by acetyl chloride (10 molar equivalents). The mixture is stirred for 1 hour at 0°–5° and 1 hour at room temperature. After removal of the solvent in vacuo, the residue is taken up in ethyl acetate and water and the pH of the aqueous layer is adjusted to 8.5 while stirring. The organic layer is removed and more ethyl acetate is added. After adjusting the pH of the aqueous layer to 2.5, the mixture is shaken thoroughly and the organic extract dried $(Na_2SO_4)$ and the solvent removed in vacuo yielding the desired product.

(D²) A molar equivalent of the cephem sulfoxide is dissolved in DMF and sodium dithionite (4 molar equivalents) is added. The mixture is cooled to 0°–5° and acetyl chloride (10 molar equivalents) is added dropwise to the reaction mixture. After stirring in the cold for 30 minutes, the mixture is worked up as described in Procedure B² yielding the desired product.

EXAMPLES 81 to 93

The following additional compounds of formula IIIa are obtained by reduction of the corresponding compounds of formula IIa by the foregoing procedure indicated in the table:

TABLE IV

Structures (IIa) and (IIIa): cephalosporin-type structures with R¹-CO-NH-, SR², CH₂X, COOH substituents.

| Example | R¹ | X | R² | Procedure |
|---|---|---|---|---|
| 81 | φCH₂— | H | CH₃ | A² |
| 82 | φCH₂— | OAc | CH₃ | A² |
| 83 | φOCH₂— | OAc | CH₃ | D² |
| 84 | CH₃CH₂ | OAc | CH₃CH₂— | C² |
| 85 | (thienyl)-CH₂- | H | CH₃ | A |
| 86 | (thienyl)-CH₂- | OAc | CH₃ | C² |
| 87 | φ-CH(OH)- | OAc | φ- | D² |
| 88 | φCH₂—O— | H | Br-φ- | A² |
| 89 | (furyl)-CH₂- | OAc | φCH₂— | A² |
| 90 | φSCH₂— | OAc | CH₃ | A² |
| 91 | (pyridyl)-CH₂- | OAc | MeO-φ- | D² |
| 92 | φ- | OAc | CH₃ | D² |
| 93 | H | H | —CH₂CH₂CH₃ | C² |

EXAMPLE 94

7-[2-Amino-2-(1,4-cyclohexadienyl)acetamido]-2-(methylthio)-cephalosporanic acid At 0°, cold trifluoroacetic acid (3 ml.) is added to a mixture of 7-[2-N-tert-butoxycarbonyl)amino-2-(1,4-cyclohexadienyl)-acetamido]-2-methylthiocephalosporanic acid (p-methoxybenzyl)-ester (500 mg.), obtained from the product of Example 33 by the procedure of Example 53, and anisole (1 ml.) and swirled for several minutes. The mixture was then kept at 25° for 15 minutes and the solvent is removed in vacuo and the residue triturated with ether. The insoluble material is dissolved in water and the pH of the solution raised to 5 by addition of Amberlite IR4B resin, while stirring vigorously. After filtering, the solution is treated with charcoal and filtered. The aqueous mixture is concentrated under reduced pressure until separation of the product 7-[2-amino-2-(1,4-cyclohexadienyl)acetamido]-2-(methylthio)cephalosporanic acid occurs, which is then collected and dried.

EXAMPLE 95

7-[2-Amino-2-(1,4-cyclohexadienyl)acetamido]-2-(methylthio)-3-desacetoxycephalosporanic acid 7-[2-N-tert-Butoxycarbonyl)amino-2-(1,4-cyclohexadienyl)-acetamido]-2-(methylthio)-3-desacetoxy cephalosporanic acid p-methoxybenzyl ester obtained from the product of Example 34 by the procedure of Example 53 is treated as described in Example 94 yielding 7-[2-amino-2-(1,4-cyclohexadienyl) acetamido]-2-(methylthio)-3-desacetoxycephalosporanic acid.

EXAMPLE 96

7-[2-Amino-2-(phenyl)acetamido]-2-(methylthio)-cephalosporanic acid

7-[2-N-tert-Butoxycarbonyl)amino-2-(phenyl)acetamido]-2-methylthiocephalosporanic acid p-methoxybenzyl ester is treated as described in Example 94 yielding 7-[2-amino-2-(phenyl)-acetamido]-2-(methylthio)cephalosporanic acid.

EXAMPLE 97

7-[2-Amino-2-(phenyl)acetamido]-2-(methylthio)-3-desacetoxycephalosporanic acid

7-[2-N-tert-Butoxycarbonyl)amino-2-(phenyl-)acetamido]-2-(methylthio)-3-desacetoxycephalosporanic acid p-methoxybenzyl ester is treated using the method described in Example 94 to yield 7-[2-amino-2-(phenyl)acetamido]-2-(methylthio)-3-desacetoxycephalosporanic acid.

EXAMPLES 98 to 111

The following additional products of formula IIIa are obtained by deesterification of the corresponding compound of formula III by the procedure indicated in the Table (see Examples 24 and 42):

TABLE V

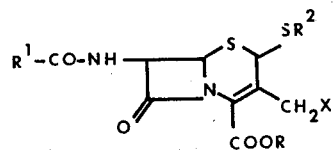
(III)

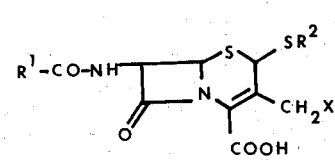
(IIIa)

| Example | $R^1$ | X | R | $R^2$ | Procedure |
|---|---|---|---|---|---|
| 98 | $\phi CH_2-$ | H | $-CH_2-\phi-OMe$ | $CH_3$ | A |
| 99 | $C_2H_5OCH_2-$ | OAc | $-CH_2-\phi-OMe$ | $CH_3$ | A |
| 100 | $\phi OCH_2-$ | OAc | $-CH_2-\phi-OMe$ | $CH_3$ | A |
| 101 | $CH_3CH_2-$ | OAc | $-CH_2-\phi-NO_2$ | $CH_3CH_2-$ | D |
| 102 | thienyl-$CH_2-$ | H | $-CH_2CCl_3$ | $CH_3$ | B |
| 103 | thienyl-$CH_2-$ | OAc | $-CH_2-\phi$ | $CH_3$ | D |
| 104 | $\phi$-CH(OH)- | OAc | $-CH_2CCl_3$ | $\phi$ | B |
| 105 | pyridyl-$CH_2-$ | OAc | $-CH_2CCl_3$ | $MeO-\phi$ | B |
| 106 | H | H | $-CH_2-\phi$ | $-CH_2CH_2CH_3$ | D |
| 107 | $\phi-$ | OAc | t-Bu | $CH_3$ | E |
| 108 | $\phi-$ | OAc | $-CH_2-\phi-NO_2$ | $Br-\phi$ | D |
| 109 | furyl-$CH_2-$ | OAc | $-CH_2-\phi-NO_2$ | $\phi CH_2$ | D |
| 110 | $\phi SCH_2-$ | OAc | $-CH_2-\phi-OMe$ | $-CH_3$ | A |
| 111 | $CH_3SCH_2-$ | OAc | $-CH_2-\phi-OMe$ | $C_2H_5$ | A |

EXAMPLE 112

2-Methylthio-7-phenylacetamidocephalosporanic acid sulfoxide

7-Phenylacetamidocephalosporanic acid sulfoxide (405 mg., 1 mmol.) is suspended in anhydrous dimethoxyethane (25 ml.) and potassium tert-butoxide (112 mg., 1 mmol.) is added while stirring at room temperature for 15 minutes under an inert atmosphere. Then trimethylchlorosilane (10 mg., 1 mmol.) is added, the mixture stirred at room temperature another 15 minutes, followed by cooling the solution to −20° to −25°. Potassium t-butoxide (1 mmol.) is added, followed by methylthiomesylate (1 mmole) to the mixture, the cold bath removed and the solution allowed to warm to room temperature. After stirring for one hour, the solvent is removed in vacuo and the residue is taken up in ethyl acetate. While stirring the organic layer with water, the pH is adjusted to 8.5, the aqueous layer is separated, ethyl acetate is added, and the pH is adjusted to 3 with dilute hydrochloric acid. The organic layer is then separated, washed with water and dried ($Na_2SO_4$). Removal of the solvent under reduced pressure yields a residue, which after chromatography on silica gel, yields 2-methylthio7-(phenylacetamido)-cephalosporanic acid sulfoxide as an amorphous solid.

EXAMPLE 113

2-Methylthio-7-(N-triphenylmethyl)amino-3-desacetoxy cephalosporanic acid sulfoxide 7-(N-Triphenylmethyl) aminodesacetoxycephalosporanic acid sulfoxide (prepared by tritylation of the corresponding 7-aminocephem carboxylate sulfoxide obtained using the method of D.C. Humber, Ger. Offen. 2,042,162 followed by removal of the protecting ester or by oxidation of 7-ADACA with sodium metaperiodate in aqueous solution) is methylthiolated by the procedure described in Example 112 to obtain 2-methylthio-7-(N-triphenylmethyl) amino-3-desacetoxycephalosporanic acid sulfoxide.

EXAMPLE 114

2-Methylthio-7-(N-triphenylmethyl) aminocephalosporanic acid sulfoxide 7-(N-Triphenylmethyl) aminocephalosporanic acid sulfoxide, prepared by the procedure described in Example 113 is methylthiolated and the product, 2-methylthio-7-(N-triphenylmethyl)-aminocephalosporanic acid sulfoxide is isolated by the procedure of Example 112.

Example 115

7-Amino-2-methylthiocephalosporanic acid sulfoxide

7-Aminocephalosporanic acid sulfoxide (288 mg., 1 mmol.) is added to anhydrous dimethoxyethane (30 ml.) under an inert atmosphere and two equivalents of bis-(trimethylsilyl) acetamide (203 mg., 1 mmol.) is added. The mixture is stirred at room temperature for four hours and then cooled to −20°. One equivalent of potassium tert-butoxide (117 mg., 1 mmol.) is added and, after stirring a few minutes to dissolve the base, methylthiomesylate (126 mg., 1 mmol.) is also added. The cold bath is removed and the mixture allowed to warm to room temperature for two hours while stirring. After removal of solvent in vacuo, the residue is taken up in ice cold water and the pH adjusted to 4.1 causing a mixture to separate from solution containing the desired 7-amino-2-methylthiocephalosporanic acid sulfoxide.

Example 116

7-Amino-2-methylthio-3-desacetoxycephalosporanic acid sulfoxide

7-Aminodesacetoxycephalosporanic acid sulfoxide is treated as described in Example 115 yielding the desired 7-amino-2-methylthio-3-desacetoxycephalosporanic acid sulfoxide.

Example 117

7-Amino-2-methylthiocephalosporanic acid sulfoxide (322 mg., 1 mmol.) is added to anhydrous dimethylformamide (10 ml.) followed by the addition of one millimole of hydrogen bromide in dry DMF. The mixture is cooled to −20° and, while stirring mechanically, phosphorous tribromide (0.2 ml.) is added and the reaction mixture stirred cold for 45 minutes. Then an ice cold solution of 10% $(NG_4)_2HPO_4$ in water (15 ml.) is added to the mixture followed by removal of solvent in vacuo. The residue is taken up in a minumum amount of water and the pH is adjusted to 4.3 causing the product, 7-amino-2-methylthiocephalosporanic acid to separate.

Example 118

7-Amino-2-methylthio-3-desacetoxycephalosporanic acid

7-Amino-2-methylthio-3-desacetoxycephalosporanic acid sulfoxide is reduced as described in Example 117 yielding 7-amino-2-methylthio-3-desacetoxycephalosporanic acid.

Example 119

2-(Methylthio)-7-[2-(2-thienyl) acetamido]cephalosporanic acid

7-Amino-2-methylthiocephalosporanic acid is acylated following the procedure described in Example 40 yielding 2-(methylthio)-7-[2-(2-thienyl)acetamido]-cephalosporanic acid as a foam.

Example 120

2-(Methylthio)-7-[2-(2-thienyl)acetamido]-3-desacetoxycephalosporanic acid

7-Amino-2-(methylthio)-3-desacetoxycephalosporanic acid is acylated with 2-(2-thienyl)acetyl chloride by the method described in Example 40 yielding 2-(methylthio)-7-[2-(2-thienyl)acetamido]-3-desacetoxycephalosporanic acid.

What is claimed is:
1. A process which comprises reacting a compound of the formula

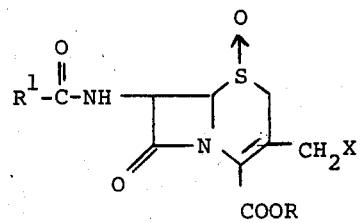

with an electrophilic compound of the formula $R^2$—S—Y or $(R^2S)_2$ in the presence of an alkali metal lower alkoxide, phenyl lithium, triphenylmethyl lithium, lithium-lower alkylamide or alkali metal hydride at a temperature in the range of about −78°C. to +30°C. thereby producing a compound of the formula

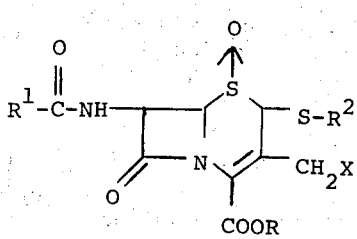

and chemically reducing the last compound with phosphorus halide, acetyl chloride-alkali metal dithionite, stannous halide or alkali metal iodide-acetyl chloride-acetic acid to obtain as a product a compound of the formula

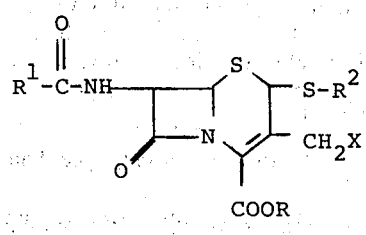

wherein in each of said formulas R is lower alkyl, lower alkoxybenzyl, nitrobenzyl, halo-lower alkyl or lower alkylsilyl; $R^1$ is hydrogen, lower alkyl, phenyl, phenyl-lower alkyl, α-aminophenyl-lower alkyl, α-hydroxyphenyl-lower alkyl, phenoxy-lower alkyl, phenylthio-lower alkyl, pyridylthio-lower alkyl, lower alkoxy-lower alkyl, lower alkylthio-lower alkyl, pyridyl-lower alkyl, thienyl, thenyl, furylmethyl, cyclo-lower alkyl-lower alkyl or α-aminocyclo-lower alkadiene-lower alkyl, said phenyl, thienyl, pyridyl, cyclo-lower alkyl and cyclo-lower alkadienyl groups being unsubstituted or substituted with one or two lower alkyl, lower alkoxy, halo, nitro, amino or trifluoromethyl groups: $R^2$ is lower alkyl, substituted lower alkyl wherein the substituent is halo or lower alkoxy, phenyl or substituted phenyl wherein the substituent is halo, lower alkoxy, nitro, cyano or carbo-lower alkoxy; X is hydroxy lower alkoxy, lower alkanoyloxy or lower alkylthio; and Y is halogen or —SO$_2$—Z wherein Z is lower alkyl, lower alkylcarbonylthio or lower alkylthio.

2. A process as in claim 1 wherein R is lower alkyl, trichloroethyl, phenyl-lower alkyl, nitrophenyl-lower alkyl or lower alkoxyphenyl-lower alkyl, $R^1$ is lower alkyl, phenyl-lower alkyl, α-aminophenyl-lower alkyl, α-hydroxyphenyl-lower alkyl, phenoxy-lower alkyl, thienylmethyl, furylmethyl, phenylthio-lower alkyl, pyridyl-lower alkyl or α-aminocyclohexadienyl-lower alkyl, $R^2$ is lower alkyl, lower alkoxy-lower alkyl, phenyl or phenyl alkoxyphenyl, X is hydrogen, lower alkanoyloxy or lower alkylthio, Y is chlorine or bromine and Z is lower alkyl or lower alkylthio.

3. A process as in claim 1 wherein R is t-butyl, trichloroethyl, benzyl, nitrobenzyl or methoxybenzyl, $R^1$ is ethyl, phenyl, benzyl, α-aminobenzyl, α-hydroxybenzyl, phenoxymethyl, thienylmethyl, furfurylmethyl, phenylthiomethyl, pyridylmethyl or α-aminocyclohexadienylmethyl, $R^2$ is methyl, ethyl, methoxymethyl, ethoxymethyl, phenyl or methoxyphenyl, X is hydrogen or acetoxy, Y is chlorine or bromine or a sulfinyl radical wherein Z is lower alkyl or lower alkylthio.

4. A process as in claim 1 comprising the additional step of removing the protective group R by treatment with p-tpluenesulfonic acid, trichloroacetic acid, formic acid, zinc or palladium-carbon.

5. A process as in claim 1 wherein the alkali metal lower alkoxide is potassium tert-butoxide and the reducing agent is phosphorous tribromide.

6. A process as in claim 4 wherein R is t-butyl, $R^1$ is phenoxymethyl, $R^2$ is methyl and X is hydrogen.

7. A process as in claim 4 wherein R is t-butyl, $R^1$ is phenoxymethyl, $R^2$ is methyl and X is acetoxy.

8. A process as in claim 4 wherein R is t-butyl, $R^1$ is thienyl, $R^2$ methyl and X is acetoxy.

9. A process as in claim 4 wherein R is t-butyl, $R^1$ is benzyl, $R^2$ is methyl and X is acetoxy.

10. A compound of the formula

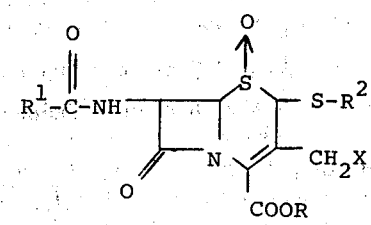

wherein R is hydrogen, lower alkyl, trichloroethyl, phenyl-lower alkyl, nitrophenyl-lower alkyl or lower alkoxyphenyl-lower alkyl; $R^1$ is hydrogen, lower alkyl, phenyl, phenyl-lower alkyl, α-aminophenyl-lower alkyl, α-hydroxyphenyl-lower alkyl, phenoxy-lower alkyl, phenylthio-lower alkyl, pyridylthio-lower alkyl, lower alkoxy-lower alkyl, lower alkylthio-lower alkyl, pyridyl-lower alkyl, thienyl, thenyl, furylmethyl, cyclo-lower alkyl-lower alkyl or α-aminocyclo-lower alkadiene-lower alkyl, said phenyl, thienyl, pyridyl, cyclo-lower alkyl and cyclolower alkadienyl groups being unsubstituted or substituted with one or two lower alkyl, lower alkoxy, halo, nitro, amino or trifluoromethyl groups; $R^2$ is lower alkyl, substituted lower alkyl wherein the substituent is halo or lower alkoxy, phenyl or substituted phenyl wherein the substituent is halo, lower alkoxy, nitro, cyano or carbo-lower alkoxy; and X is hydrogen, lower alkoxy, lower alkanoyloxy or lower alkylthio.

11. A compound as in claim 10 wherein R is t-butyl, trichloroethyl, benzyl, nitrobenzyl or methoxybenzyl; $R^1$ is ethyl, phenyl, benzyl, α-aminobenzyl, α-hydroxybenzyl, phenoxymethyl, thienylmethyl, furfurylmethyl, phenylthiomethyl, pyridymethyl or α-aminocyclohexadienylmethyl; $R^2$ is methyl, ethyl, methoxymethyl, ethoxymethyl, phenyl or methoxyphenyl; and X is hydrogen or acetoxy.

12. A compound as in claim 10 wherein R is t-butyl; $R^1$ is phenoxymethyl; $R^2$ is methyl; and X is hydrogen.

13. A compound as in claim 10 wherein R is t-butyl; $R^1$ is phenoxymethyl; $R^2$ is methyl; and X is acetoxy.

14. A compound as in claim 10 wherein R is t-butyl; $R^1$ is thienyl; $R^2$ is methyl; and X is acetoxy.

15. A compound as in claim 10 wherein R is t-butyl; $R^1$ is benzyl; $R^2$ is methyl; and X is acetoxy.

16. A compound of the formula

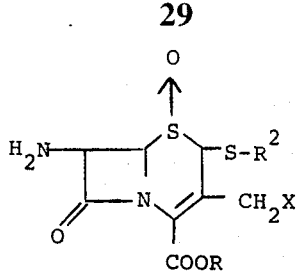

wherein R is hydrogen, lower alkyl, trichloroethyl, phenyl-lower alkyl, nitrophenyl-lower alkyl or lower alkoxy-phenyl-lower alkyl; $R^2$ is lower alkyl, lower alkoxy-lower alkyl, phenyl or phenyl-lower alkoxyphenyl; and X is hydrogen, lower alkanoyloxy or lower alkylthio.

17. A compound as in claim 16 wherein R is t-butyl, trichloroethyl, benzyl, nitrobenzyl or methoxybenzyl; $R^1$ is ethyl, phenyl, benzyl, α-aminobenzyl, α-hydroxybenzyl, phenoxymethyl, thienylmethyl, furfurylmethyl, phenylthiomethyl, pyridylmethyl or α-aminocyclohexadienylmethyl; $R^2$ is methyl; ethyl, methoxymethyl, ethoxymethyl, phenyl or methoxyphenyl; and X is hydrogen or acetoxy.

18. A compound as in claim 16 wherein R is p-methoxy benzyl, $R^2$ is methyl and X is acetoxy.

19. A compound as in claim 16, wherein R is t-butyl, $R^2$ is methyl and X is acetoxy.

* * * * *